US012096736B2

(12) United States Patent
Moldenhauer

(10) Patent No.: US 12,096,736 B2
(45) Date of Patent: Sep. 24, 2024

(54) RICE CULTIVAR CLL18

(71) Applicant: The Board of Trustees of the University of Arkansas, Little Rock, AR (US)

(72) Inventor: Karen A. K. Moldenhauer, Garnavillo, IA (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 184 days.

(21) Appl. No.: 17/853,403

(22) Filed: Jun. 29, 2022

(65) Prior Publication Data

US 2024/0000033 A1 Jan. 4, 2024

(51) Int. Cl.
*A01H 5/10* (2018.01)
*A01H 6/46* (2018.01)

(52) U.S. Cl.
CPC ............ *A01H 6/4636* (2018.05); *A01H 5/10* (2013.01)

(58) Field of Classification Search
None
See application file for complete search history.

(56) References Cited

U.S. PATENT DOCUMENTS 7,351,891 B2 4/2008 Sarreal et al.
7,642,434 B2 1/2010 Moldenhauer
8,841,525 B2 9/2014 Linscombe
9,399,778 B2 * 7/2016 Moldenhauer ..... C12N 15/8277
11,160,230 B2 11/2021 Sha
11,160,231 B2 11/2021 Sha
11,206,784 B1 12/2021 Moldenhauer

OTHER PUBLICATIONS

Moldenhauer, K. A. K., et al. 2007. Registration of 'Wells' rice. Crop Sci. 47:442-443.
Moldenhauer, K.A.K., et al. 2010. Roy J, high yielding stiff-strawed, long-grain rice variety. In R.J. Norman, and K.A.K. Moldenhauer (eds.) Rice Research Studies 2009. University of Arkansas Agricultural Experiment Station Research Series 581. pp. 53-59.
U.S. Plant Variety Protection Application No. 202300067 filed Dec. 1, 2022, Rice Cultivar CLL18, The Board of Trustees of the University of Arkansas.

* cited by examiner

*Primary Examiner* — Jason Deveau Rosen
(74) *Attorney, Agent, or Firm* — Quarles & Brady, LLP

(57) ABSTRACT

A rice cultivar designated CLL18 is disclosed herein. The present invention provides seeds, plants, and plant parts derived from rice cultivar CLL18. Further, it provides methods for producing a rice plant by crossing CLL18 with itself or another rice variety. The invention also encompasses any rice seeds, plants, and plant parts produced by the methods disclosed herein, including those in which additional traits have been transferred into CLL18 through the introduction of a transgene or by breeding CLL18 with another rice cultivar.

32 Claims, No Drawings

RICE CULTIVAR CLL18

BACKGROUND OF THE INVENTION

The present invention relates to a new and distinctive rice cultivar, designated 'CLL18.'

Rice is an ancient agricultural crop and is today one of the principal food crops of the world. There are two cultivated species of rice: *Oryza sativa* L., the Asian rice, and *O. glaberrima* Steud., the African rice. *O. sativa* L. constitutes virtually all the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valleys of California.

Rice is a semi-aquatic crop that benefits from flooded soil conditions during part or all of the growing season. In the United States, rice is grown on flooded soils to optimize grain yields. Heavy clay soils or silt loam soils with hard pan layers about 30 cm below the surface are preferred rice-producing soils because they minimize water losses from soil percolation. Rice production in the United States can be broadly categorized as either dry-seeded or water-seeded. In the dry-seeded system, rice is sown into a well-prepared seed bed with a grain drill or by broadcasting the seed and incorporating it with a disk or harrow. Moisture for seed germination is provided by irrigation or rainfall. Alternatively, the seed may be broadcast by airplane into a flooded field, which is promptly drained following seeding. With the dry-seeded system, when the plants have reached sufficient size (four- to five-leaf stage), a shallow permanent flood of water, 5 to 16 cm deep, is applied to the field for the remainder of the crop season.

In the water-seeded system, rice seed is soaked for 12 to 36 hours to initiate germination, and the seed is broadcast by airplane into a flooded field. The seedlings emerge through a shallow flood, or the water may be drained from the field for a short period of time to enhance seedling establishment. A shallow flood is maintained until the rice approaches maturity. For both the dry-seeded and water-seeded production systems, the fields are drained when the crop is mature, and the rice is harvested 2 to 3 weeks later with large combines. In rice breeding programs, breeders typically employ the production systems that are predominant in their region. Thus, a drill-seeded breeding nursery is typically used by breeders in a region where rice is drill-seeded and a water-seeded nursery is typically used in regions where water-seeding is prominent.

Rice in the United States is classified into three primary market types by grain size, shape, and chemical composition of the endosperm: long-grain, medium-grain, and short-grain. Typical U.S. long-grain cultivars cook dry and fluffy when steamed or boiled, whereas medium and short-grain cultivars cook moist and sticky. Traditionally, in the southern states, long-grain cultivars have been grown and generally receive higher market prices.

Rice, *Oryza sativa* L., is an important and valuable field crop. A continuing goal of plant breeders is to produce stable, high yielding rice cultivars that are agronomically sound. To accomplish this goal, rice plants with traits that result in superior cultivars must be developed.

SUMMARY OF THE INVENTION

The present invention provides a novel rice cultivar designated CLL18. The invention encompasses the seeds, plants, and plant parts of rice cultivar CLL18, as well as plants with all of the physiological and morphological characteristics of CLL18.

In another aspect, the present invention provides methods for controlling weeds in the vicinity of a rice plant of rice cultivar CLL18 using an acetohydroxyacid synthase (AHAS)-inhibiting herbicide. In some embodiments, seeds of rice cultivar CLL18 are treated with an AHAS-inhibiting herbicide. In other embodiments, the herbicide is applied post-emergence.

This invention also provides methods for producing a rice plant by planting a plurality of seeds or by crossing rice CLL18 with itself or another rice line. Any plant breeding methods using rice cultivar CLL18 are part of this invention, including selfing, backcrosses, hybrid production, and crosses to populations. All plants and seeds produced using rice cultivar CLL18 as a parent are within the scope of this invention, including gene-converted plants of CLL18. Methods for introducing a gene into CLL18, either through traditional breeding, transformation or gene editing, are provided herein.

In still another aspect, the present invention provides regenerable cells for use in tissue culture of rice plant CLL18, as well as rice plants regenerated from these tissue cultures.

Definitions

To provide a clear and consistent understanding of the specification and claims, the following definitions are provided:

Allele. One of two or more alternative forms of a gene, all of which relate to a single trait or characteristic. In a diploid cell or organism, two alleles of a given gene occupy corresponding loci on a pair of homologous chromosomes.

Apparent amylose content. The amount of starch in the endosperm of milled rice that is amylose, provided in g/kg herein. Amylose content varies depending on the growth environment of the rice. It is an important grain characteristic used to describe cooking behavior.

Backcrossing. A process in which a breeder repeatedly crosses hybrid progeny back to a parental line. For example, a first generation (F1) hybrid may be crossed with one of the parental lines used to produce the F1 hybrids.

Breeding. The genetic manipulation of living organisms.

Cell. A cell is the basic structural unit of all organisms. As used herein, this term includes isolated cells, cells grown in tissue culture, and cells that comprise a plant or plant part.

Cultivar. Used interchangeably with "variety." Refers to plants with the characteristics of a particular genotype or combination of genotypes. Plants of a particular cultivar are distinguished from any other plant grouping by at least one characteristic.

Days to 50% heading. The average number of days from emergence to the day when 50% of all panicles are exerted at least partially through the leaf sheath. A measure of maturity.

Embryo. The plant embryo is the part of a seed or bud that contains the earliest forms of the new plant's roots, stem, and leaves.

F #. Denotes a filial generation, wherein the # is the generation number. For example, F1 is the first filial generation.

Gene. Refers to a unit of inheritance corresponding to a distinct DNA sequence that forms part of a chromosome. A gene may encode a polypeptide or a functional nucleic acid molecule.

Gene-converted. Describes a plant wherein essentially all of the desired morphological and physiological characteristics of a parental variety are maintained with the exception of a single trait that was transferred into the variety via backcrossing or genetic engineering.

Genotype. Refers to the genetic constitution of a cell or organism.

Grain yield. Measured in pounds per acre at 12.0% moisture content. The grain yield of rice is determined by the number of panicles per unit area, the number of fertile florets per panicle, and the grain weight per floret.

Haploid. A cell or organism having a single set of unpaired chromosomes.

Head rice. Kernels of milled rice in which greater than ¾ of the kernel is unbroken.

Herbicide resistant. Describes a plant that is tolerant or resistant to an herbicide at a level that would normally kill or inhibit the growth of a normal or wild-type rice plant.

Hybrid. Refers to the progeny of genetically dissimilar plant parents or to stock produced by controlled cross-pollination, as opposed to a non-hybrid seed produced by natural pollination.

Lodging. The percentage of plant stems that are leaning or have fallen to the ground before harvest. Lodging is determined by visual scoring, in which crops are rated from 0% (all plants standing) to 100% (all plant in plot lying flat on the soil surface). Lodged plants are difficult to harvest and reduce yield and grain quality. Lodging resistance is also called "straw strength".

Milling yield. The total amount of rice kernels (including both whole and broken kernels) recovered after milling (i.e., removal of hulls, bran, and germ). In contrast, "head rice yield" is the amount of whole kernels recovered after milling. Both values are expressed as a weight percentage of the original paddy or rough rice sample that was milled. Milling quality is often presented as a ratio of head rice yield to total rice yield. For example, for a sample of 100 grams of rough rice, a milling yield of 65:70 indicates that 65 grams of head rice and 70 grams of total milled rice were produced.

Pedigree. Refers to the lineage or genealogical descent of a plant.

Plant. As used herein, the term "plant" includes plant cells, plant protoplasts, and plant cell tissue cultures from which rice plants can be regenerated; plant calli, plant clumps and plant cells that are intact in plants; and parts of plants, such as embryos, pollen, ovules, flowers, glumes, panicles, leaves, stems, roots, root tips, anthers, and pistils.

Plant height. Measured in centimeters from the soil surface to the tip of the extended panicle at harvest.

Plant parts. Includes, without limitation, protoplasts, leaves, stems, roots, root tips, anthers, pistils, seeds, grains, embryos, pollen, ovules, cotyledons, hypocotyls, pods, flowers, shoots, tissues, petioles, cells, and meristematic cells.

Progeny. Includes an F1 rice plant produced from the cross of two rice plants, as well as plants produced from subsequent generational crosses (e.g., F2, F3, F4, F5, F6, F7, F8, F9, and F10) with the recurrent parental line.

Regeneration. Refers to the development of a plant from tissue culture.

Seeds. Includes seeds and plant propagules of all kinds including, but not limited to, true seeds, seed pieces, suckers, corms, bulbs, fruit, tubers, grains, cuttings, cut shoots, and the like. However, in preferred embodiments, it refers to true seeds.

Trait. Refers to an observable and/or measurable characteristic of an organism. For example, the present invention describes plants that have a trait that make them resistant to acetohydroxyacid synthase (AHAS) inhibiting herbicides.

Transgenic. Describes an organism or cell that contains genetic material that has been artificially introduced.

Wild-type. Used to refer to a gene that is common throughout a population and is, thus, arbitrarily designated the "normal" or "wild-type" form of the gene.

DETAILED DESCRIPTION OF THE INVENTION

The present invention provides a novel rice cultivar designated CLL18. The invention encompasses both the seeds of this cultivar and plants grown from these seeds.

Development and Characterization of Rice Cultivar CLL18

Rice cultivar CLL18 (*Oryza sativa* L.), is a very high yielding, short season, long-grain Clearfield® rice cultivar that comprises a gene for resistance to Newpath® herbicide. CLL18 originated from the cross 'Roy J'/'CL142-AR' (cross no. 20113023), which was made in 2011. Roy J is a high yielding stiff strawed line that was released in 2010. CL142-AR is a Clearfield® cultivar that was released in 2009 and has increased resistance to acetohydroxyacid synthase (AHAS) inhibiting herbicides, i.e. imidazolinone herbicides. A timeline outlining how CLL18 was developed is provided in Table 1. The herbicide resistance trait of CLL18 is discussed further in the section titled "Herbicide Resistance" below.

TABLE 1

CLL18 development timeline

| Year | Program stage |
|---|---|
| 2021 | Rice was subjected to Arkansas Rice Performance Trials (ARPT) (6 locations) and Pre Commercial Trial (PC), in which it was treated with 3 times the rate of 16 oz NEWPATH ®/acre in a post application between the 3-leaf and 2-tiller stage. Breeder head row and 2 acre increase were grown and treated with 3 times the rate of 16 oz Newpath ®/acre in a post application between the 3-leaf and 2-tiller stage in Stuttgart, AR. Seed was produced for possible release. |
| 2020-21 | Winter: Breeder head row (one half of panicle) were grown in Puerto Rico and were treated with NEWPATH ® herbicide to produce seed for future testing and seed increase. |
| 2020 | Rice was subjected to Arkansas Rice Performance Trials (ARPT) (5 locations), Uniform Regional Rice Nursery (URRN) (5 locations), and the IMI ARPT, in which it was treated with 3 times the rate of 16 NEWPATH ®/acre in a post application between the 3-leaf and 2-tiller stage. Panicles were selected from the IMI ARPT for breeder head row and the seed from IMI ARPT was used as the seed source for the following year in the ARPT and URRN. |

TABLE 1-continued

CLL18 development timeline

| Year | Program stage |
|---|---|
| 2019 | Summer: The IMI Stuttgart Initial Test (IMI SIT) was performed in Stuttgart, AR (STG18IMI01-121). Rice was treated with 3 times the rate of 16 oz NEWPATH ®/acre in a post application between the 3-leaf and 2-tiller stage. The plots that were used for future seed were rogued heavily and checked for off-types. |
| 2018 | Summer: $F_8$ panicle row was grown in Stuttgart, AR (IMI-01-121) and was treated with 3 times the rate of 16 oz NEWPATH ®/acre in a post application between the 3-leaf and 2-tiller stage. |
| 2017 | Summer: $F_7$ panicle row was grown in Stuttgart, AR (IMI-02-244) and was treated with 3 times the rate of 16 oz NEWPATH ®/acre in a post application between the 3-leaf and 2-tiller stage. |
| 2016 | Summer: $F_6$ panicle row was grown in Stuttgart, AR (IMI-02-090) and was treated with 3 times the rate of 16 oz NEWPATH ®/acre in a post application between the 3-leaf and 2-tiller stage. |
| 2015 | Summer: $F_5$ panicle row was grown in Stuttgart, AR (IMI-03-138) and was treated with 3 times the rate of 16 oz NEWPATH ®/acre in a post application between the 3-leaf and 2-tiller stage. |
| 2014 | Summer: $F_4$ panicle row was grown in Stuttgart, AR (IMI-07-143) and was treated with 3 times the rate of 16 oz NEWPATH ®/acre in a post application between the 3-leaf and 2-tiller stage. |
| 2013 | Summer: $F_3$ panicle row was grown in Stuttgart, AR (IMI-11-253) and was treated with 3 times the rate of 16 oz NEWPATH ®/acre in a post application between the 3-leaf and 2-tiller stage. |
| 2012 | Summer: F2 plants were grown in a field in Lonoke, AR (LK-P4-4) and were treated with 3 times the rate of 16 oz NEWPATH ®/acre in a post application at the 3-4 leaf stage. |
| 2011-12 | Winter: F1 plants were grown in the greenhouse in Stuttgart, AR. |
| 2011 | Summer: Cross # 20113023, Roy J/CL142-AR |

The experimental designation for early evaluation of CLL18 was STG18IMI-01-121, starting with a bulk of $F_8$ seed from the 2018 panicle row IMI-01-121. CLL18 was tested in the Arkansas Rice Performance Trials (ARPT) in 2020-2021 and in the Cooperative Uniform Regional Rice Nursery (URRN) in 2020-2021 as entry RU2001093 (Note: RU indicates that the trial was the URRN; 20 indicates that the year entered was 2020; 01 indicates that the location was Stuttgart, AR; and 093 indicates the entry number). The results of these performance trials for CLL18 are compared to those for other rice cultivars in the section titled "Performance Trial Results" below.

CLL18 matures approximately 2 days later than 'CLL15'. CLL18 is a standard statured variety with an approximate 37-inch canopy height, which is similar to 'Diamond', and 44-inch plant height. CLL18 has strong straw strength, which is an indicator of lodging resistance, as rated in the 2019 Clearfield Stuttgart Initial Test and the 2020 ARPT, CLARPT, and 2020 URRN (in which only one test experienced lodging for this line). On a relative straw strength scale (0=very strong straw, 5=very weak straw based on percent lodging) CLL18, CLL15, 'CLL16', and Diamond, rated 1.2, 1.0, 1.0, and 1.0, respectively. CLL18 has a lodging resistance rating of 2 on scale of 1-5 (1=erect, 5=flat), whereas Roy J has a rating of 1. The nitrogen fertilizer requirements of CLL18 are 135 pounds/acre.

CLL18 has excellent rough rice yields that are as good or better than any of the other pure line cultivars. Its 2-year [2020-2021] mean yield in the ARPT was 221 bushels/acre, which compares favorably to CLL16 at 209 bushels/acre. Rough rice grain yields of CLL18 ranked with Diamond in the 2020-2021 ARPT. In 9 ARPT tests (2020-2021), CLL18, CLL15, CLL16, RT 7512 FP, RT XP753, and Diamond averaged yields of 220, 209, 210, 237, 244 and 209 bushels/acre, respectively. Data from the URRN conducted in Stuttgart, AR and Crowley, LA in 2020-2021, showed that CLL18 has an average grain yield of 224 bushels/acre, which compares favorably to RU1801145, CLL15, CLL16, and Diamond which have average grain yields of 213, 204, 219, and 204 bushels/acre, respectively. In the 2021 Pre-Commercial Test CLL18, CLL16, CLL17, and Diamond yielded 222, 213, 181, and 211 bushels/acre, respectively. Milling yields (mg $g^{-1}$ whole kernel:mg $g^{-1}$ total milled rice) at 120 mg $g^{-1}$ moisture from the 2020 ARPT averaged 590:690, 610:700, 610:690, 590:690, and 600:700 for CLL18, RU1801145, CLL15, CLL16 and Diamond, respectively.

CLL18 has a very good disease package, better than any other of the other Clearfield lines. It has the blast resistance gene Pi-km and is susceptible to common rice blast (*Pyricularia grisea* (Cooke) Sacc) in Arkansas conditions, Similar to Diamond. Its moderately susceptible to sheath blight (*Rhizoctonia solani* Kuhn), which compares favorably with CLL15, CLL16, and Diamond, which are susceptible. Like Diamond, its moderately susceptible to bacterial panicle blight (*Burkholderia glumae* or other *Burkholderia* species), which compares favorably to the susceptible cultivars CLL15 and CLL16. It is susceptible to false smut (*Ustilaginoidea virens*

(Cooke) Takah) and is moderately resistant to narrow brown leaf spot (*Cerospora oryzae*). The disease ratings of CLL18 are compared to those of other rice cultivars in the section titled "Disease Evaluations" below.

Plants of CLL18 have erect culms, green erect leaves, and glabrous lemma, palea, and leaf blades. The lemma and palea are straw colored with straw colored apiculi at maturity. CLL18 has nice long plump kernels, with a grain size, averaging 7.38 mm for the 5 locations of the 2020 ARPT, as compared to RU1801145, CLL15, CLL16, RT XP753, and Diamond at 7.27, 7.29, 7.37, 7.31 and 7.23 mm/kernel, respectively. Individual milled kernel weights of CLL18, RU1801145, CLL15, CLL16, RT XP573, and Diamond averaged 21.8, 22.2, 20.6, 22.7, 22.2, and 21.6 mg/kernel, respectively.

The endosperm of CLL18 is non-glutinous, nonaromatic, and covered by a light brown pericarp. Rice quality parameters indicate that CLL18 has typical southern U.S. long-grain rice cooking quality characteristics as described by Webb et al., "Utilization Characteristics and Qualities of United States Rice," in: Rice Grain Quality and Marketing (p. 25-35, IRRI, Manila, Philippines, 1985). Based on the results of the 2020 ARPT from Riceland Foods Inc Quality Laboratory, CLL18 has an average apparent starch amylose content of 23.4, as compared to RU1801145, CLL15, CLL16, RT XP753, and Diamond, at 22.9, 21.3, 22.8, 19.8, and 22.3 g $kg^{-1}$, respectively. CLL18 has an intermediate gelatinization temperature of 69.5° C., as compared to RU1801145, CLL15, CLL16, RT XP753, and Diamond, at 69.3° C., 69.7° C., 69.2° C., 70.9° C., and 69.6° C., respectively.

The breeder seed field of CLL18 was rogued several times throughout the season. The variants that may be found in the release include any combination of the following: taller, shorter, earlier, later, glabrous or pubescent plants, as well as intermediate or very-long slender grains. Other atypical plants may still be encountered in the variety. The total variants and/or off-types numbered less than 1 per 2000 plants.

Performance Trial Results

TABLE 2

2020 Arkansas Rice Performance Trials (Stuttgart, RREC; Keiser, NEREC; Clay County; Desha County; Pine Tree, PTRS)

| VARIETY | Avg. Grain Yield | Avg. Plant Ht.[b] (in.) | Avg. 50% Heading (days) | Avg. Straw Strength | Avg. Test Wt. (lbs.) | HR-TR[a] |
|---|---|---|---|---|---|---|
| CLL18 | 217 | 37.1 | 82 | 1.0 | 41.4 | 59:69 |
| RU1801145 | 204 | 38.6 | 83 | 1.2 | 41.6 | 61:70 |
| CLL15 | 200 | 32.7 | 81 | 1.0 | 41.9 | 61:69 |
| CLL16 | 205 | 37.9 | 85 | 1.2 | 40.6 | 59:69 |
| RT 7521 FP | 226 | 39.6 | 81 | 2.6 | 42.3 | 61:71 |
| RT XP 753 | 239 | 38.0 | 80 | 1.0 | 42.8 | 60:72 |
| Diamond | 208 | 37.0 | 83 | 1.0 | 41.3 | 60:70 |

[a]HR-TR is head rice:total milled rice
[b]Plant height is provided as canopy height, not to tip of panicle

TABLE 3

2021 Arkansas Rice Performance Trials (Stuttgart, RREC; Keiser, NEREC; Clay County; Desha County; and Pine Tree, PTRS)

| VARIETY | Avg. Grain Yield | Avg. Plant Ht.[b] (in.) | Avg. 50% Heading (days) | Avg. Straw Strength | Avg. Test Wt. (lbs.) | HR-TR[a] |
|---|---|---|---|---|---|---|
| CLL18 | 224 | 38.3 | 92 | 1.0 | 41.9 | |
| RU1801145 | 214 | 40.3 | 95 | 1.3 | 41.9 | |
| CLL15 | 213 | 33.2 | 91 | 1.2 | 40.6 | |
| CLL16 | 214 | 37.7 | 96 | 1.0 | 43.7 | |
| RT 7521 FP | 248 | 38.3 | 91 | 2.0 | 38.8 | |
| RT XP753 | 254 | 36.8 | 89 | 1.0 | 40.0 | |
| Diamond | 204 | 37.4 | 93 | 1.3 | 40.7 | |

[a]HR-TR is head rice: total milled rice
[b]Plant height is provided as canopy height, not to tip of panicle

TABLE 4

2020-2021 ARPT data

| VARIETY* | YIELD (BU/AC) | HEIGHT (IN.) | MATURITY (50% HD) | MILLING HR:TOT |
|---|---|---|---|---|
| CLL18 | 221 | 37.7 | 87 | |
| RU1801145 | 209 | 39.3 | 89 | |
| CLL15 | 207 | 33.0 | 86 | |
| CLL16 | 210 | 37.8 | 91 | |
| RT 7521 FP | 237 | 39.0 | 86 | |
| RT XP 753 | 247 | 37.4 | 85 | |
| Diamond | 206 | 37.2 | 88 | |

TABLE 5

2020 ARPT means by location

| | GRAIN YIELD (BU/AC)[a] | | | | | | HEAD RICE (%) - TOTAL RICE (%) | | | | | |
|---|---|---|---|---|---|---|---|---|---|---|---|---|
| VARIETY | CLAY | DESHA | NEREC | PTRS | RREC | MEAN | CLAY | DESHA | NEREC | PTRS | RREC | MEAN |
| CLL18 | 260 | 227 | 212 | 197 | 186 | 217 | 57:70 | 57:68 | 59:69 | 59:69 | 62:70 | 59:69 |
| RU1801145 | 255 | 210 | 203 | 184 | 170 | 204 | 59:70 | 59:69 | 62:70 | 59:70 | 64:71 | 61:70 |
| CLL15 | 238 | 183 | 191 | 190 | 199 | 200 | 61:70 | 60:69 | 62:69 | 62:69 | 62:69 | 61:69 |
| CLL16 | 257 | 205 | 203 | 185 | 178 | 205 | 53:69 | 56:68 | 61:69 | 60:69 | 63:70 | 59:69 |
| RT 7521 FP | 261 | 211 | 212 | 249 | 196 | 226 | 61:72 | 60:70 | 59:70 | 63:71 | 63:71 | 61:71 |
| RT XP 753 | 290 | 263 | 219 | 225 | 196 | 239 | 61:73 | 62:72 | 61:71 | 59:72 | 59:71 | 60:72 |
| Diamond | 270 | 226 | 190 | 183 | 169 | 208 | 59:71 | 58:70 | 62:71 | 60:70 | 61:70 | 60:70 |

[a]Yield trials in 2018, Clay County Farmers Field (CLAY); Desha County Farmers Field (DESHA); Northeast Research and Extension Center, (NEREC), Keiser, AR; Pine Tree Research Station, (PTRS), Colt, AR; and Rice Research and Extension Center, (RREC), Stuttgart, AR

TABLE 6

2021 ARPT means by location

| | GRAIN YIELD (BU/AC)[a] | | | | | | | HEAD RICE (%):TOTAL; RICE (%) | | | | | | |
|---|---|---|---|---|---|---|---|---|---|---|---|---|---|---|
| VARIETY | RREC | NEREC | PTES | NERice[b] | CLAY | DESHA[b] | AVG | RREC | NEREC | PTES | NERice | CLAY | DESHA | AVG |
| CLL18 | 223 | 247 | 194 | 237 | 234 | 207 | 224 | | | | | | | |
| RU1801145 | 214 | 245 | 200 | 225 | 230 | 169 | 214 | | | | | | | |
| CLL15 | 206 | 218 | 184 | 240 | 234 | 198 | 213 | | | | | | | |
| CLL16 | 216 | 220 | 180 | 229 | 241 | 195 | 214 | | | | | | | |
| RT 7521 FP | 248 | 244 | 234 | 289 | 250 | 222 | 248 | | | | | | | |
| RT XP753 | 251 | 263 | 227 | 249 | 282 | 252 | 254 | | | | | | | |
| Diamond | 220 | 238 | 179 | 194 | 226 | 165 | 204 | | | | | | | |

[a]Yield trials in 2021, Rice Research & Extension Center (RREC), Stuttgart, AR; Northeast Research and Extension Center, (NEREC), Keiser, AR; Pine Tree Research Station, (PTRS), Colt, AR; and Clay County Farmer Field, (CLAY);
[b]Northeast Rice Research Station (NERice), Jonesboro, AR; and Desha County Farmer Field (DESHA) not in mean

TABLE 7

2020-2021 ARPT means by location

| | GRAIN YIELD (BU/AC)[a] | | | | | | HEAD RICE (%) - TOTAL RICE (%) | | | | | |
|---|---|---|---|---|---|---|---|---|---|---|---|---|
| VARIETY | CLAY | DESHA | NEREC | PTRS | RREC | MEAN | CLAY | DESHA | NEREC | PTRS | RREC | MEAN |
| CLL18 | 247 | 217 | 230 | 196 | 205 | 219 | | | | | | |
| RU1801145 | 243 | 190 | 224 | 192 | 192 | 208 | | | | | | |
| CLL15 | 236 | 191 | 205 | 287 | 203 | 224 | | | | | | |
| CLL16 | 249 | 200 | 212 | 183 | 197 | 208 | | | | | | |
| RT 7521 FP | 256 | 217 | 228 | 242 | 222 | 233 | | | | | | |
| RT XP 753 | 286 | 258 | 241 | 226 | 224 | 247 | | | | | | |
| Diamond | 248 | 196 | 214 | 181 | 195 | 207 | | | | | | |

[a]Yield trials in 2020 and 2021, Clay County Farmer Field, (CLAY); Desha County Farmer Field (DESHA); Northeast Research and Extension Center, (NEREC), Keiser, AR; Pine Tree Research Station, (PTRS), Colt, AR; Rice Research and Extension Center, (RREC), Stuttgart, AR.

TABLE 8

2019 Clearfield Stuttgart Initial Test, Stuttgart, AR (3 replications)

| VARIETY | YIELD (Bu/Ac) | DAYS TO 50% HEAD | HEIGHT (in) | TEST WEIGHT | LODGING % | % HEAD:% TOTAL |
|---|---|---|---|---|---|---|
| CLL18 | 216 | 83 | 43 | 38.7 | 0 | 44:68 |
| CLL15 | 183 | 81 | 39 | 40.5 | 0 | 52:70 |
| CLL16 | 214 | 86 | 43 | 39.6 | 0 | 48:68 |
| GEMINI 214 | 233 | 81 | 45 | 37.2 | 0 | 39:70 |

TABLE 9

2020 Clearfield Arkansas Rice Performance Trial, Stuttgart, AR (3 replications)

| VARIETY | YIELD (Bu/Ac) | DAYS TO 50% HEAD | HEIGHT (in) | TEST WEIGHT | LODGING % | % HEAD:% TOTAL |
|---|---|---|---|---|---|---|
| CLL18 | 229 | 87 | 44 | 38.0 | 0 | 54:67 |
| RU1801145 | 217 | 86 | 47 | 37.8 | 0 | 60:69 |
| CLL16 | 213 | 88 | 47 | 38.2 | 0 | 54:67 |
| RT 7231 FP | 230 | 81 | 48 | 38.7 | 0 | 56:72 |

TABLE 10

2020 URRN yield and agronomic data collected from Stuttgart, AR and Crowley, LA

| | YIELD (lbs/acre) | | | DAYS TO 50% HEADING | | | PLANT HEIGHT (in) | | | LODGING[a] % | | |
|---|---|---|---|---|---|---|---|---|---|---|---|---|
| VARIETY | AR | LA | AVG | AR | LA | AVG | AR | LA | AVG | AR | LA | AVG |
| CLL18 | 231 | 200 | 216 | 93 | 98 | 95 | 46 | 41 | 44 | 50 | 0 | 16 |
| RU1801145 | 216 | 199 | 208 | 92 | 100 | 96 | 47 | 43 | 45 | 37 | 0 | 7 |
| CLL15 | 165 | 226 | 196 | 89 | 96 | 93 | 40 | 35 | 38 | 0 | 0 | 13 |
| CLL16 | 204 | 213 | 209 | 95 | 103 | 99 | 44 | 41 | 43 | 0 | 0 | 0 |
| DIAMOND | 196 | 216 | 206 | 93 | 93 | 93 | 44 | 39 | 42 | 20 | 0 | 4 |

[a]Percent of plot lodged

TABLE 11

2021 URRN yield and agronomic data collected from Stuttgart, AR and Crowley, LA

| | YIELD (lbs/acre) | | | DAYS TO 50% HEADING | | | PLANT HEIGHT (in) | | | LODGING[a] % | | |
|---|---|---|---|---|---|---|---|---|---|---|---|---|
| VARIETY | AR | LA | AVG | AR | LA | AVG | AR | LA | AVG | AR | LA | AVG |
| CLL18 | 260 | 205 | 233 | 91 | 94 | 93 | 46 | 41 | 44 | 0 | 0 | 0 |
| RU1801145 | 253 | 182 | 218 | 89 | 95 | 92 | 47 | 40 | 44 | 0 | 0 | 0 |
| CLL15 | 228 | 196 | 212 | 89 | 92 | 91 | 40 | 38 | 39 | 0 | 0 | 0 |
| CLL16 | 239 | 220 | 230 | 91 | 94 | 93 | 43 | 40 | 42 | 0 | 0 | 0 |
| DIAMOND | 238 | 167 | 203 | 88 | 92 | 90 | 44 | 39 | 42 | 0 | 0 | 0 |

[a]Percent of plot lodged

TABLE 12

2020-2021 URRN yield and agronomic data

| | YIELD (lbs/acre) | | | DAYS TO 50% HEADING | | | PLANT HEIGHT (in) | | | LODGING[a] % | | |
|---|---|---|---|---|---|---|---|---|---|---|---|---|
| VARIETY | AR | LA | AVG | AR | LA | AVG | AR | LA | AVG | AR | LA | AVG |
| CLL18 | 246 | 203 | 224 | 92 | 96 | 94 | 46 | 41 | 44 | 25 | 0 | 12.5 |
| RU1801145 | 235 | 191 | 213 | 91 | 98 | 94 | 47 | 42 | 45 | 19 | 0 | 9.5 |
| CLL15 | 197 | 211 | 204 | 89 | 94 | 92 | 40 | 37 | 39 | 0 | 0 | 0 |
| CLL16 | 222 | 216 | 219 | 93 | 99 | 96 | 44 | 40 | 43 | 0 | 0 | 0 |
| DIAMOND | 217 | 192 | 204 | 91 | 93 | 92 | 44 | 39 | 42 | 10 | 0 | 5 |

[a]Percent of plot lodged

TABLE 13

Riceland ARPT quality data 2020

| Test | | | | Satake | | Chalk | Length | Width | Thickness | L:W | Weight |
|---|---|---|---|---|---|---|---|---|---|---|---|
| Title | Loc | REP | Cultivar | Whiteness | MD | (%) | (mm) | (mm) | (mm) | Ratio | (g) |
| ARPT | Clay | 1 | CLL18 | 41.0 | 99 | 2.74 | 7.33 | 2.15 | 1.76 | 3.41 | 0.0216 |
| ARPT | Clay | 3 | CLL18 | 43.9 | 113 | 2.07 | 7.40 | 2.08 | 1.73 | 3.56 | 0.0222 |
| ARPT | DESHA | 1 | CLL18 | 44.5 | 115 | 4.24 | 7.56 | 2.13 | 1.74 | 3.55 | 0.0221 |
| ARPT | DESHA | 3 | CLL18 | 40.3 | 94 | 4.05 | 7.32 | 2.12 | 1.72 | 3.45 | 0.0209 |
| ARPT | NEREC | 1 | CLL18 | 45.8 | 120 | 3.67 | 7.47 | 2.11 | 1.76 | 3.54 | 0.0221 |
| ARPT | NEREC | 3 | CLL18 | 45.8 | 125 | 4.21 | 7.37 | 2.16 | 1.72 | 3.41 | 0.0213 |
| ARPT | PTRS | 1 | CLL18 | 47.3 | 129 | 2.70 | 7.34 | 2.04 | 1.73 | 3.60 | 0.0217 |
| ARPT | PTRS | 3 | CLL18 | 45.9 | 123 | 5.26 | 7.22 | 2.10 | 1.71 | 3.44 | 0.0205 |
| ARPT | RREC | 1 | CLL18 | 43.6 | 114 | 1.67 | 7.40 | 2.14 | 1.75 | 3.46 | 0.0228 |
| ARPT | RREC | 3 | CLL18 | 43.8 | 116 | 3.84 | 7.38 | 2.09 | 1.75 | 3.53 | 0.0223 |

TABLE 13-continued

| Riceland ARPT quality data 2020 | | | | | | | | | | | | |
|---|---|---|---|---|---|---|---|---|---|---|---|---|
| Test | | | | Satake | | Chalk | Length | Width | Thickness | L:W | Weight |
| Title | Loc | REP | Cultivar | Whiteness | MD | (%) | (mm) | (mm) | (mm) | Ratio | (g) |
| | | AVERAGE | | 44.2 | 115 | 3.44 | 7.38 | 2.11 | 1.74 | 3.49 | 0.0218 |
| | | MINIMUM | | 40.3 | 94 | 1.67 | 7.22 | 2.04 | 1.71 | 3.41 | 0.0205 |
| | | MAXIMUM | | 47.3 | 129 | 5.26 | 7.56 | 2.16 | 1.76 | 3.60 | 0.0228 |

TABLE 14

| Riceland ARPT quality data 2020 (CONTINUED) | | | | | | | | | | | | |
|---|---|---|---|---|---|---|---|---|---|---|---|---|
| Test | | | | Gel Temp | Amylose | Moisture | RVA (rvu units) | | | | |
| Title | Loc | REP | Cultivar | (° C.) | (%) | (%) | Peak | Trough | Breakdown | Final | Setback |
| ARPT | Clay | 1 | CLL18 | 68.71 | 27.26 | 10 | 214 | 111 | 103 | 248 | 34 |
| ARPT | Clay | 3 | CLL18 | 68.93 | 23.84 | 11 | 228 | 125 | 104 | 261 | 33 |
| ARPT | DESHA | 1 | CLL18 | 70.03 | 23.59 | 9 | 246 | 123 | 123 | 272 | 26 |
| ARPT | DESHA | 3 | CLL18 | 70.44 | 21.36 | 11 | 234 | 131 | 104 | 281 | 47 |
| ARPT | NEREC | 1 | CLL18 | 69.07 | 22.14 | 10 | 234 | 111 | 123 | 248 | 15 |
| ARPT | NEREC | 3 | CLL18 | 68.87 | 23.85 | 11 | 226 | 103 | 123 | 245 | 18 |
| ARPT | PTRS | 1 | CLL18 | 69.47 | 23.94 | 10 | 241 | 113 | 128 | 251 | 10 |
| ARPT | PTRS | 3 | CLL18 | 69.76 | 25.48 | 10 | 236 | 126 | 110 | 270 | 34 |
| ARPT | RREC | 1 | CLL18 | 70.13 | 20.07 | 10 | 234 | 111 | 123 | 240 | 6 |
| ARPT | RREC | 3 | CLL18 | 69.90 | 22.70 | 10 | 233 | 118 | 115 | 249 | 16 |
| | | AVERAGE | | 69.53 | 23.42 | 10 | 233 | 117 | 116 | 257 | 24 |
| | | MINIMUM | | 68.71 | 20.07 | 9 | 214 | 103 | 103 | 240 | 6 |
| | | MAXIMUM | | 70.44 | 27.26 | 11 | 246 | 131 | 128 | 281 | 47 |

TABLE 15

| Riceland Laboratory ARPT quality data 2020 means | | | | | | | | | |
|---|---|---|---|---|---|---|---|---|---|
| | | Satake | | | | | | | |
| Cultivar | AVG | Whiteness | Milling Degree | Moisture (%) | Chalk (%) | Length (mm) | Width (mm) | Thickness (mm) |
| CLL18 | Avg | 44.2 | 114.8 | 10.11 | 3.44 | 7.38 | 2.11 | 1.74 |
| RU1801145 | Avg | 45.6 | 122.3 | 10.20 | 2.79 | 7.27 | 2.20 | 1.76 |
| CLL15 | Avg | 44.9 | 114.4 | 10.13 | 2.57 | 7.29 | 2.14 | 1.65 |
| CLL16 | Avg | 45.0 | 120.7 | 9.93 | 1.70 | 7.37 | 2.19 | 1.72 |
| RT XP 753 | Avg | 46.0 | 121.6 | 9.98 | 2.99 | 7.31 | 2.13 | 1.71 |
| Diamond | Avg | 44.3 | 114.3 | 10.13 | 2.25 | 7.23 | 2.12 | 1.72 |

TABLE 16

| Riceland Laboratory ARPT quality data 2020 means (CONTINUED) | | | | | | | | | | |
|---|---|---|---|---|---|---|---|---|---|---|
| | | L:W | Weight | Gel Temp | Amylose | RVA (rvu) | | | | |
| Cultivar | AVG | Ratio | (mg) | (° C.) | (%) | Peak | Trough | Breakdown | Final | Setback |
| CLL18 | Avg | 3.49 | 21.8 | 69.53 | 23.42 | 233 | 117 | 116 | 257 | 24 |
| RU1801145 | Avg | 3.31 | 22.2 | 69.30 | 22.89 | 237 | 122 | 115 | 263 | 26 |
| CLL15 | Avg | 3.41 | 20.6 | 69.72 | 21.33 | 230 | 111 | 120 | 261 | 31 |
| CLL16 | Avg | 3.37 | 22.7 | 69.19 | 22.78 | 236 | 122 | 114 | 260 | 24 |
| RT XP 753 | Avg | 3.44 | 22.2 | 70.88 | 19.79 | 244 | 119 | 125 | 258 | 14 |
| Diamond | Avg | 3.41 | 21.6 | 69.55 | 22.31 | 236 | 114 | 122 | 254 | 18 |

TABLE 17

Riceland Laboratory Clearfield Stuttgart Initial Test quality data 2019 means

| TEST | VARIETY | Chalk % | Length mm | Width mm | Thickness mm | L:W ratio | Weight g | Gel Temp ° C. | Amylose % |
|---|---|---|---|---|---|---|---|---|---|
| CL SIT | CLL18 | 2.32 | 7.26 | 2.12 | 1.75 | 3.43 | 0.0212 | 70.78 | 20.81 |
| CL SIT | CLL15 | 1.63 | 7.19 | 2.11 | 1.69 | 3.41 | 0.0207 | 70.65 | 20.38 |
| CL SIT | CLL16 | 1.90 | 7.33 | 2.20 | 1.75 | 3.34 | 0.0237 | 71.14 | 20.64 |
| CL SIT | GEMINI 214 | 3.77 | 7.08 | 2.11 | 1.70 | 3.36 | 0.0204 | 71.62 | 18.67 |

Disease Evaluations

Most rice diseases are rated visually on a 0-9 scale to estimate degree of severity. Numerical data are often converted to this scale. A rating of zero indicates no disease. A rating of one to three indicates resistance where little loss may occur. Conversely, a nine rating indicates maximum disease, which typically results in a susceptible reaction and hence, substantial yield loss in severe disease epidemic situations. Depending upon the disease in question, a disease rating of four to six is usually indicative of acceptable disease resistance under conditions slightly favoring the pathogen. Numerical ratings are sometimes converted to letter symbols where 0-3=R (resistant), 3-4=MR (moderately resistant), 5-6=MS (moderately susceptible) 7=S (susceptible) and 8-9 VS (very susceptible). Exceptions to established ratings may occur unexpectedly as disease situations change. It is not unusual for ratings to vary across locations and years due to environmental differences and research procedures. Ratings within a source traditionally have been consistent.

Nurseries are also established in growers' fields across the state to evaluate disease reactions in production fields using producers' practices. Over time these nurseries document variety performance under different disease conditions in Arkansas production fields.

Below, Tables 17-18 present the disease evaluation data collected for CLL18 by Dr. Wamishe.

TABLE 17

Summary of available leaf blast rating data from plants inoculated with the indicated race using standard greenhouse techniques, 2020, three replicates

| | IB-1 | IB-17 | IB-49 | IC-17 | IE-1K |
|---|---|---|---|---|---|
| Greenhouse leaf blast ratings | 5, 5, 5 | 5, 6, 6 | 6, 5, 6 | 6, 5, 5 | 4, 0, 0 |

TABLE 18

Rice variety reactions[1] to diseases, 2020

| Cultivar | Sheath Blight | Blast | Straight head | Bacterial Panicle Blight | Narrow Brown Leaf Spot | Kernel Smut | False Smut | Black Sheath Rot |
|---|---|---|---|---|---|---|---|---|
| CLL18 | MS | S | | MS | MR | | S | |
| CLL16 | S | MS/MR | | S | MR | | MS | |
| 'CL111' | VS | MS | S | VS | S | S | S | S |
| 'CL151' | S | VS | VS | VS | S | S | S | S |
| 'CL153' | S | MS | MS | MS | S | S | S | |
| CLL15 | S | MS | MS | S | S | S | S | |
| 'CLL17' | S | MS | | | | | | |
| Diamond | S | S | MS | MS | MS | S | VS | S |
| Jewel | MS | MS | S | R | | MS | MS | |
| Roy J | MS | S | S | S | R | VS | S | MS |
| RT 7521 FP | S | R | R | MR | MS | MS | S | S |
| RT XP753 | MS | R | MS | MR | MR | MS | S | S |
| RT GEMINI 214 CL | S | MR | R | | | MS | VS | |
| 'Wells' | S | S | S | S | S | S | S | MS |

[1]Reaction: R = Resistant; MR = Moderately Resistant; MS = Moderately Susceptible; S = Susceptible; VS = Very Susceptible. Reactions were determined based on historical and recent observations from test plots and in grower fields across Arkansas. In general, these reactions would be expected under conditions that favor severe disease development including excessive nitrogen rates (most diseases) or low flood depth (blast).

Greenhouse blast tests are the primary means of screening large number of entries for varietal reaction to the common blast races occurring in the production areas. Although results are quite variable and testing conditions tend to overwhelm any field resistance that may be present in the rice, this test provides an accurate definition of the fungus by variety genetics. Blast field nurseries utilize natural and lab produced inoculum to better define their resistance under field conditions. Field nurseries are established and artificially inoculated to provide a uniform disease pressure for evaluations under field conditions.

Herbicide Resistance

Clearfield® (CL) rice is resistant to imidazolinone herbicides (WSSA Group 2), which control weeds by inhibiting the enzyme acetohydroxyacid synthase (AHAS), also called acetolactate synthase (ALS). CL rice was developed through mutagenesis of the ALS locus using traditional breeding techniques and is not considered genetically modified. The herbicide-resistance trait of this rice makes it particularly useful in regions where there is a need to control weedy rice and other tough grasses. Thus, the majority of rice cultivars planted in the southern United States are CL inbred or hybrid.

The plants of rice cultivar CLL18 have increased tolerance or resistance to AHAS-inhibiting herbicides, particularly imidazolinone herbicides. Thus, the plants of rice cultivar CLL18 are herbicide-tolerant or herbicide-resistant rice plants. An "herbicide-tolerant" or a "herbicide-resistant" rice plant is a rice plant that is tolerant or resistant to at least one herbicide at a level that would normally kill, or inhibit the growth of, a normal or wild-type rice plant. For the present invention, the terms "herbicide-tolerant" and "herbicide-resistant" are used interchangeably and are intended to have an equivalent meaning and an equivalent scope. Similarly, the terms "herbicide-tolerance" and "herbicide-resistance" are used interchangeably and are intended to have an equivalent meaning and an equivalent scope. Likewise, the terms "imidazolinone-tolerant" and "imidazolinone-resistant" are used interchangeably and are intended to be of an equivalent meaning and an equivalent scope as the terms "imidazolinone-tolerance" and "imidazolinone-resistance", respectively.

Accordingly, the present invention also provides rice seeds treated with an AHAS-inhibiting herbicide. AHAS-inhibiting herbicides include, without limitiation, imidazolinone herbicide, a sulfonylurea herbicide, a triazolopyrimidine herbicide, a pyrimidinyloxybenzoate herbicide, a sulfonylamino-carbonyltriazolinone herbicide, and a mixture thereof. However, in preferred embodiments, the AHAS-inhibiting herbicide is an imidazolinone herbicide or a mixture of two or more imidazolinone herbicides. Suitable imidazolinone herbicides include, without limitation, NEWPATH® (imazethapyr), PURSUIT (imazethapyr), CADRE (imazapic), RAPTOR (imazamox), SCEPTER (imazaquin), ASSERT (imazethabenz), ARSENAL (imazapyr), a derivative of any of the aforementioned herbicides, and a mixture of two or more of the aforementioned herbicides, for example, imazapyr/imazamox (ODYSSEY). More specifically, the imidazolinone herbicide can be selected from, but is not limited to, 2-(4-isopropyl-4-methyl-5-oxo-2-imidiazolin-2-yl)-nicotinic acid, [2-(4-isopropyl)-4-][methyl-5-oxo-2-imidazolin-2-yl)-3-quinolinecarboxylic]acid, [5-ethyl-2-(4-isopropyl-]4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, [2-(4-isopropyl-4-methyl-5-oxo-2-]imidazolin-2-yl)-5-methylnicotinic acid, and a mixture of methyl[6-(4-isopropyl-4-]methyl-5-oxo-2-imidazolin-2-yl)-m-toluate and methyl[2-(4-isopropyl-4-methyl-5-]oxo-2-imidazolin-2-yl)-p-toluate.

A wide variety of formulations can be employed for protecting plants from weeds to enhance plant growth and reduce competition for nutrients. Customary formulations include solutions, emulsions, suspensions, dusts, powders, pastes and granules. The use form depends on the particular intended purpose. However, in each case, it should ensure a fine and even distribution of the compound.

The herbicide may be applied at pre-emergence, post-emergence, pre-planting or at planting to control weeds in areas surrounding the rice plants described herein. The herbicide and herbicide formulations can be applied in accordance with conventional methods, for example, by spraying, irrigation, dusting, or the like. In some embodiments, the herbicide is applied by contacting the rice seeds before sowing and/or after pregermination with an AHAS-inhibiting herbicide. In other embodiments, the herbicide is applied to the weeds and to the rice plant applied post-emergence, e.g., using over-the-top application.

An herbicide can be used by itself or an herbicide formulation can be used that contains other additives. The herbicide can also be used as a seed treatment. Additives that may be found in an herbicide formulation include other herbicides, detergents, adjuvants, spreading agents, sticking agents, stabilizing agents, or the like. The herbicide formulation can be a wet or dry preparation and can include, but is not limited to, flowable powders, emulsifiable concentrates and liquid concentrates. Such formulations are prepared in a known manner, for example by extending the active compound with auxiliaries suitable for the formulation of agrochemicals, such as solvents and/or carriers, emulsifiers, surfactants and dispersants, preservatives, antifoaming agents, anti-freezing agents, and also optionally colorants and/or binders and/or gelling agents.

Methods

This present invention provides methods for producing rice plants. In some embodiments, these methods involve planting a plurality of rice seeds provided herein under conditions favorable for the growth of rice plants.

The plants of rice cultivar CLL18 have increased resistance to AHAS-inhibiting herbicides, particularly imidazolinone herbicides, and thus find use in methods for controlling weeds. Accordingly, the present invention provides methods for controlling weeds in the vicinity of a rice plant of rice cultivar CLL18. The AHAS-inhibiting herbicide may be selected from the group consisting of an imidazolinone herbicide, a sulfonylurea herbicide, a triazolopyrimidine herbicide, a pyrimidinyloxybenzoate herbicide, a sulfonylamino-carbonyltriazolinone herbicide, or a mixture thereof. However, in preferred embodiments, the AHAS-inhibiting herbicide is an imidazolinone herbicide or a mixture of two or more imidazolinone herbicides.

The herbicide may be applied using any application method known in the art including, but not limited to, seed treatment, soil treatment, and foliar treatment. In some embodiments, the herbicide is applied by contacting the rice seeds with the herbicide. The term "contacting" signifies that the active ingredient of the herbicide is on the surface of the seed at the time of application, though a greater or lesser amount of the ingredient may penetrate into the seed, depending on the method of application. Suitable seed treatment techniques include, without limitation, seed dressing, seed coating, seed dusting, seed soaking, and seed pelleting. In some embodiments, the herbicide is applied to the seeds before sowing and/or after pregermination. "Pregermination" refers to a process in which seeds are sprouted in the absence of soil. Thus, the phrase "after pregermination" refers to the period of development after germination has occurred (i.e., after the root penetrates through the seed coat).

In other embodiments, the herbicide is applied to the weeds and to the rice plant post-emergence, i.e., after the weeds and crop have emerged from the soil. These treatments either can be applied in a broadcast or directed fashion. Notably, for post-emergence applications it is often advantageous to combine the herbicide with a surfactant to facilitate maximum coverage of the weed with the solution. Additives found in an imidazolinone herbicide formulation include other herbicides, detergents, adjuvants, spreading agents, sticking agents, stabilizing agents, or the like. The herbicide formulation can be a wet or dry preparation and can include, but is not limited to, flowable powders, emulsifiable concentrates, and liquid concentrates. The herbicide and herbicide formulations can be applied in accordance with conventional methods, for example, by spraying, irrigation, dusting, or the like.

For the methods of the present invention, the preferred amount or concentration of the herbicide is an "effective amount" or "effective concentration", i.e., an amount or concentration that is sufficient to kill or inhibit the growth of a similar wild-type rice plant, rice plant tissue, rice plant cell, or rice seed, but that does not kill or inhibit as severely the growth of the herbicide-resistant plants, plant tissues, plant cells, and seeds. Typically, the effective amount of an herbicide is an amount that is routinely used in agricultural production systems to kill weeds of interest. Such amounts are known to those of ordinary skill in the art. Herbicide application rates generally range from 0.1 g to 10 kg of the active ingredient per 100 kg of seed, preferably from 1 g to 5 kg per 100 kg of seed, in particular from 1 g to 2.5 kg per 100 kg of seed. The phrase "control of undesired vegetation" refers to the killing of weeds and/or otherwise retarding or inhibiting the normal growth of the weeds. A "weed" is any plant that grows in locations where it is undesired. The weeds may include, for example, dicotyledonous and monocotyledonous weeds. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus*, and *Taraxacum*. Monocotyledonous weeds include, but are not limited to, weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus*, and *Apera*. In addition, the weeds of the present invention can include crop plants that are growing in an undesired location. For example, a soybean plant that is in a field that predominantly comprises rice plants can be considered a weed, if the soybean plant is undesired in the field of rice plants. Another example of a weed is red rice, which is the same species as cultivated rice.

In these methods, the AHAS-inhibiting herbicide can be applied by any method known in the art including, but not limited to, seed treatment, soil treatment, and foliar treatment. Prior to application, the AHAS-inhibiting herbicide can be converted into the customary formulations, for example solutions, emulsions, suspensions, dusts, powders, pastes, and granules. The use form depends on the particular intended purpose. However, in each case, the use form should ensure a fine and even distribution of the active herbicide compound. The formulations are prepared in a known manner (see, e.g., U.S. Pat. No. 3,060,084, EP-A 707 445 (for liquid concentrates), Browning, "Agglomeration", Chemical Engineering, pp. 147-48 (Dec. 4, 1967); Perry's Chemical Engineer's Handbook, 4th Ed., McGraw-Hill, New York, pp. 8-57 (1963), and et seq.; PCT Publication No. WO 91/13546; U.S. Pat. Nos. 4,172,714; 4,144,050; 3,299,566; 3,920,442; 5,180,587; 5,232,701; and 5,208,030; G.B. Patent No. 2,095,558; Klingman, "Weed Control as a Science", John Wiley and Sons, Inc., New York (1961); Hance et al., Weed Control Handbook, 8th Ed., Blackwell Scientific Publications, Oxford (1989); Mollet, H., Grubemann, A., Formulation technology, Wiley VCH Verlag GmbH, Weinheim, Germany (2001); and D. A. Knowles, Chemistry and Technology of Agrochemical Formulations, Kluwer Academic Publishers (ISBN 0-7514-0443-8), Dordrecht (1998)), for example by extending the active compound with auxiliaries suitable for the formulation of agrochemicals, such as solvents and/or carriers, and, if desired, emulsifiers, surfactants and dispersants, preservatives, antifoaming agents, anti-freezing agents, colorants, binders, and/or gelling agents.

Examples of suitable solvents include water, aromatic solvents (e.g., Solvesso products, xylene), paraffins (e.g., mineral oil fractions), alcohols (e.g., methanol, butanol, pentanol, benzyl alcohol), ketones (e.g., cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used. Examples of suitable carriers are ground natural minerals (e.g., kaolins, clays, talc, chalk) and ground synthetic minerals (e.g., highly disperse silica, silicates). Suitable emulsifiers are nonionic and anionic emulsifiers (e.g., polyoxyethylene fatty alcohol ethers, alkylsulfonates, arylsulfonates). Examples of dispersants are lignin-sulfite waste liquors and methylcellulose.

Suitable surfactants used are alkali metal, alkaline earth metal, and ammonium salts (e.g., of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids, and sulfated fatty alcohol glycol ethers), condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors, and methylcellulose.

Substances that are suitable for the preparation of directly sprayable solutions, emulsions, pastes, or oil dispersions include mineral oil fractions of medium to high boiling point (e.g., kerosene or diesel oil); coal tar oils and oils of vegetable or animal origin; aliphatic, cyclic, and aromatic hydrocarbons (e.g., toluene, xylene, paraffin, tetrahydronaphthalene, alkylated naphthalenes or their derivatives), methanol, ethanol, propanol, butanol, cyclohexanol, cyclohexanone, isophorone, highly polar solvents (e.g., dimethyl sulfoxide, N-methylpyrrolidone), and water. Additional substances that can be added to the formulation include anti-freezing agents (e.g., glycerin, ethylene glycol, and propylene glycol) and bactericides. Suitable antifoaming agents include, for example, antifoaming agents based on silicon or magnesium stearate. Suitable preservatives include, for example, dichlorophen and enzylalkoholhemiformal. Seed treatment formulations may additionally comprise binders and optionally colorants.

Binders can be added to improve the adhesion of the active materials on the seeds after treatment. Suitable binders include, for example, block copolymers EO/PO surfactants but also polyvinylalcohols, polyvinylpyrrolidones, polyacrylates, polymethacrylates, polybutenes, polyisobutylenes, polystyrene, polyethyleneamines, polyethyleneamides, polyethyleneimines (LUPASOL, POLYMIN), polyethers, polyurethans, polyvinylacetate, tylose, and copolymers derived from these polymers.

Optionally, colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, and basic red 108. An example of a suitable gelling agent is carrageen (SATIAGEL).

Powders, materials for spreading, and dustable products can be prepared by mixing or concomitantly grinding the active substances with a solid carrier. Granules (e.g., coated granules, impregnated granules, and homogeneous granules) can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers (e.g., ammonium sulfate, ammonium phosphate, ammonium nitrate), urea, and products of vegetable origin (e.g., cereal meal, tree bark meal, wood meal, nutshell meal, cellulose powders).

In general, the formulations comprise the AHAS-inhibiting herbicide at a concentration of from 0.01% to 95% by weight of active compound, preferably from 0.1 to 90% by weight. In this case, the AHAS-inhibiting herbicides are employed in a purity of 90% to 100% by weight, preferably 95% to 100% by weight (according to NMR spectrum). For seed treatment purposes, formulations can be diluted 2-10 fold leading to concentrations in the range of 0.01% to 60% by weight of active compound, preferably 0.1 to 40% by weight.

The AHAS-inhibiting herbicide can be used in the form of directly sprayable solutions, powders, suspensions or dispersions, emulsions, oil dispersions, pastes, dustable products, materials for spreading, or granules, by means of spraying, atomizing, dusting, spreading or pouring the herbicide formulation. The optimal use form depends on the intended purpose. Aqueous use forms can be prepared from emulsion concentrates, pastes or wettable powders (e.g., sprayable powders, oil dispersions) by adding water. To prepare emulsions, pastes, or oil dispersions, the substances, as such or dissolved in an oil or solvent, can be homogenized in water by means of a wetter, tackifier, dispersant or emulsifier. However, it is also possible to prepare concentrates that are suitable for dilution with water composed of active substance, wetter, tackifier, dispersant or emulsifier and, if appropriate, solvent or oil.

The active compound concentrations in the ready-to-use preparations can be varied within a relatively wide range. In general, the active compounds are concentrations are from 0.0001% to 10% by weight, preferably from 0.01% to 1% by weight. The AHAS-inhibiting herbicide may also be used successfully in the ultra-low-volume process (ULV), it being possible to apply formulations comprising over 95% by weight of active compound, or even to apply the active compound without additives.

This present invention also provides methods for producing a rice seed or plant by crossing a first parent rice plant with a second parent rice plant, wherein either the first or second parent rice plant is of the line CLL18. In some embodiments, a breeding cross is made to introduce new genetics into the CLL18 progeny (as opposed to a self or a sib cross, made to select among existing genetic alleles). In these embodiments, a population of hybrid rice plants will be produced that, on average, derive 50% of their alleles from cultivar CLL18. The resulting first generation (F1) hybrid rice seeds may be harvested and used to grow plants that express a subset of characteristics from CLL18. Alternatively, a plant of this population may be selected and repeatedly selfed or sibbed with a rice cultivar resulting from successive filial generations. In other embodiments, both the first and second parent rice plants can come from the rice cultivar CLL18. However, advantageously, the rice cultivar is used in crosses with other, different, rice cultivars to produce F1 rice seeds and plants with superior characteristics. In some embodiments, the rice cultivar CLL18 is crossed with a second rice plant that is transgenic. Rice cultivar CLL18 may also be crossed with other species, including those of the family Graminaceae, and especially of the genera *Zea, Tripsacum, Croix, Schlerachne, Polytoca, Chionachne*, and *Trilobachne*, of the tribe Maydeae. See the section below titled "Breeding Methods" for a detailed description of breeding techniques that may utilized with the present invention.

In some embodiments, a CLL18 progeny plant is selected that has molecular markers, morphological characteristics, and/or physiological characteristics in common with CLL18. Techniques such as restriction fragment length polymorphism (RFLP)-enhanced selection, genetic marker enhanced selection (e.g., SSR markers), and the making of double haploids may be utilized to identify progeny that share particular traits with CLL18.

Further, this invention provides methods for introducing a desired trait into rice cultivar CLL18. This may be accomplished using traditional breeding methods, such as backcrossing. Here, rice cultivar CLL18 is crossed with a second rice line expressing the desired trait and progeny with both the desired trait and characteristics of CLL18 are selected and crossed. These steps are repeated until plants with both the desired trait and essentially all the physiological and morphological characteristics of CLL18 have been produced.

Alternatively, the desired trait may be introduced by transforming the rice cultivar with a transgene. The transgene may confer at least one trait selected from the following: herbicide resistance; insect resistance; resistance to bacterial, fungal, or viral disease; modified fatty acid metabolism; modified carbohydrate metabolism; and male sterility. See the section below titled "Transformation Methods" for a detailed description of transformation techniques that may utilized with the present invention. The transgenic cultivar produced by these methods may be crossed with another cultivar to produce a new transgenic cultivar. Alternatively, the transgene incorporated by these methods could be moved into another cultivar using traditional backcrossing techniques.

Optionally, any of the disclosed methods may further comprise additional steps involving producing rice seed from the resulting rice plants and/or planting the rice seed.

The present invention encompasses all plants, or parts thereof, produced by the methods described herein, as well as the seeds produced by these plants. Further, any plants derived from rice cultivar CLL18 or produced from a cross using cultivar CLL18 are provided. This includes genetic variants, created either through traditional breeding methods or through transformation, as well as plants produced in a male-sterile form. Notably, this includes gene-converted plants developed by backcrossing. Any of the seeds, plants, or plant parts provided may be utilized for human food, livestock feed, and as a raw material in industry.

The present invention also encompasses progeny of rice cultivar CLL18 comprising a combination of at least two CLL18 traits selected from those listed in the Tables and Detailed Description of the Invention, wherein the progeny rice plant is not significantly different from CLL18 for said traits as determined at the 5% significance level when grown in the same environment. One of skill in the art knows how to compare a trait between two plant varieties to determine if there is a significant difference between them (Fehr and Walt, Principles of Cultivar Development, pp. 261-286 (1987)). Molecular markers or mean trait values may be used to identify a plant as progeny of CLL18. Alternatively, progeny may be identified through their filial relationship with rice cultivar CLL18 (e.g., as being within a certain number of breeding crosses of rice cultivar CLL18). For example, progeny produced by the methods described herein may be within 1, 2, 3, 4, or 5 breeding crosses of rice cultivar CLL18.

Tissue Culture

The present invention provides tissue cultures of regenerable cells or protoplasts produced from rice cultivar CLL18. As is well known in the art, tissue culture of rice can be used for the in vitro regeneration of a rice plant. Thus, such cells and protoplasts may be used to produce plants having the physiological and morphological characteristics of rice cultivar CLL18. The rice plants regenerated by these methods are also encompassed by the present invention.

As used herein, the term "tissue culture" describes a composition comprising isolated cells or a collection of such cells organized into parts of a plant. Exemplary tissues for culture include protoplasts, calli, plant clumps, and plant cells that can be grown in culture, or parts of plants, such as embryos, pollen, flowers, seeds, pods, leaves, stems, roots, root tips, and anthers. Culture of various rice tissues and regeneration of plants therefrom is well known in the art.

Breeding Methods

The goal of rice breeding is to develop new, superior rice cultivars and hybrids. A superior cultivar is produced when a new combination of desirable traits is formed within a single plant variety. Desirable traits may include higher seed yield, resistance to diseases and insects, better stems and roots, tolerance to low temperatures, and better agronomic characteristics or grain quality.

The breeding methods used with the present invention may involve a single-seed descent procedure, in which one seed per plant is harvested and used to plant the next generation. Alternatively, the methods may utilize a multiple-seed procedure, in which one or more seeds harvested from each plant in a population is threshed together to form a bulk which is used to plant the next generation.

Use of rice cultivar CLL18 in any plant breeding method is encompassed by the present invention. The choice of a breeding or selection method will depend on several factors, including the mode of plant reproduction, the heritability of the trait(s) being improved, and the type of cultivar used commercially (e.g., F1 hybrid cultivar, pureline cultivar). Popular selection methods include pedigree selection, modified pedigree selection, mass selection, recurrent selection, backcrossing, or a combination thereof.

Pedigree selection is commonly used for the improvement of self-pollinating crops. Two parents are crossed to produce an F1 population. An F2 population is produced by selfing one or several F1's. Selection of the best individuals may begin in the F2 population; then, beginning in the F3 generation, the best individuals in the best families are selected. Replicative testing of families can begin in the F4 generation to make selection of traits with low heritability more effective. At an advanced stage of inbreeding (e.g., F6 or F7), the best lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population, which is often subjected to additional cycles of selection.

Backcrossing is commonly used to transfer genes for highly heritable traits into a desirable homozygous cultivar or inbred line. The term "backcrossing" refers to the repeated crossing of hybrid progeny back to one of the parental plants, referred to as the recurrent parent. The plant that serves as the source of the transferred trait is called the donor parent. After the initial cross, individuals possessing the transferred trait are selected and repeatedly crossed to the recurrent parent. The resulting plant is expected to have the attributes of the recurrent parent along with the trait transferred from the donor parent.

Transformation Methods

As is noted above, the present invention provides plants and seeds of rice cultivar CLL18 in which additional traits have been transferred. While such traits may be selected for using traditional breeding methods, they may also be introduced as transgenes. "Transgenes" include both foreign genes and additional or modified versions of native genes. Plants can be genetically engineered to have a wide variety of traits of agronomic interest including, without limitation, male sterility, waxy starch, herbicide resistance, resistance for bacterial, fungal, or viral disease, insect resistance, male fertility, enhanced nutritional quality, industrial usage, yield stability, and yield enhancement. Many examples of genes that confer such traits have been described in the literature and are well known in the art. In certain preferred embodiments, the transgene confers resistance to an herbicide selected from the group consisting of: glyphosate, sulfonylurea, imidazolinone, dicamba, glufosinate, phenoxy proprionic acid, L-phosphinothricin, cyclohexone, cyclohexanedione, triazine, 2,4-Dichlorophenoxyacetic acid, hydroxyphenyl-pyruvate dioxygenase (HPPD) inhibitors, and benzonitrile.

Transgenes are typically introduced in the form of an expression vector. As used herein, an "expression vector" is DNA comprising a gene operatively linked to a regulatory element (e.g., a promoter). The expression vector may contain one or more such gene/regulatory element combinations. The expression vector may also include additional sequences, such as a signal sequence or a tag, that modify the protein produced by the transgene. In some embodiments, the vector as a plasmid.

Expression vectors include at least one genetic marker operably linked to a regulatory element (e.g., a promoter) that allows transformed cells containing the vector to be recovered by selection. In some embodiments, negative selection (i.e., inhibiting growth of cells that do not contain the selectable marker gene) it utilized. Negative selection markers include, for example, genes that result in detoxification of a chemical agent (e.g., an antibiotic or an herbicide) and genes that result in insensitivity to an inhibitor. Exemplary negative selection genes include neomycin phosphotransferase II (nptII), hygromycin phosphotransferase, gentamycin acetyl transferase, streptomycin phosphotransferase, and aminoglycoside-3'-adenyl transferase. In other embodiments, positive selection (i.e., screening for the product encoded by a reporter gene) is utilized. Exemplary reporter genes include β-glucuronidase, β-galactosidase, luciferase, chloramphenicol acetyltransferase, and green fluorescent protein (GFP).

Transgene expression is typically driven by operably linking the transgene to a promoter within the expression vector. However, other regulatory elements may also be used to drive expression, either alone or in combination with a promoter. As used herein, a "promoter" is a region of DNA upstream of a transcription start site that is involved in recognition and binding of RNA polymerase for transcription initiation. Any class of promoter may be selected to drive the expression of a transgene. For example, the promoter may be "tissue-specific," "cell type-specific," "inducible," or "constitutive". Those of skill in the art know how to select a suitable promoter based the particular circumstances and genetic engineering goals.

Methods for producing transgenic plants are well known in the art. General descriptions of plant expression vectors, reporter genes, and transformation protocols can be found in Gruber, et al., "Vectors for Plant Transformation", in *Methods in Plant Molecular Biology & Biotechnology* in Glich, et al., (Eds. pp. 89-119, CRC Press, 1993). General methods of culturing plant tissues are provided for example by Maki et al., "Procedures for Introducing Foreign DNA into Plants" in *Methods in Plant Molecular Biology & Biotechnology*, Glich et al., (Eds. pp. 67-88 CRC Press, 1993); and by Phillips et al., "Cell-Tissue Culture and In-Vitro Manipulation" in *Corn & Corn Improvement,* 3rd Edition; Sprague et al., (Eds. pp. 345-387 American Society of Agronomy Inc., 1988). Methods of introducing expression vectors into plant tissue include direct gene transfer methods, such as microprojectile-mediated delivery, DNA injection, and electroporation, as well as the direct infection or co-cultivation of plant cells with *Agrobacterium tumefaciens*, described for example by Horsch et al., *Science,* 227:1229 (1985). Descriptions of *Agrobacterium* vector systems and methods for *Agrobacterium*-mediated gene transfer are provided by Gruber et al., supra.

DEPOSIT INFORMATION

A deposit of the University of Arkansas Division of Agriculture Rice Research and Extension Center proprietary rice cultivar CLL18 disclosed above and recited in the appended claims has been made with the Provasoli-Guillard National Center for Marine Algae and Microbiota (NCMA) (60 Bigelow Drive, East Boothbay, ME 04544). The date of deposit was May 1, 2023. The deposit of 625 seeds was taken from the same deposit maintained by the University of Arkansas Division of Agriculture Rice Research and Extension Center (P.O. 2900 Hwy 130 E., Stuttgart, AR 72160) since prior to the filing date of this application. All restrictions will be irrevocably removed upon granting of a patent, and the deposit is intended to meet all of the requirements of 37 C.F.R. §§ 1.801-1.809. The Accession Number provided by the International Depositary Authority is 11202305002.

The deposit will be maintained in the depository for a period of thirty years, or five years after the last request, or for the enforceable life of the patent, whichever is longer, and will be replaced as necessary during that period.

What is claimed is:

1. A rice seed of the cultivar CLL18, a representative sample of seed of said cultivar having been deposited under National Center for Marine Algae and Microbiota International Depositary Authority Accession No. 202305002.

2. The rice seed of claim 1, wherein said seed is treated with an agronomically acceptable seed treatment composition.

3. The rice seed of claim 2, wherein said seed is treated with an acetohydroxyacid synthase (AHAS)-inhibiting herbicide.

4. The rice seed of claim 3, wherein said AHAS-inhibiting herbicide is selected from the group consisting of imidazolinone herbicides, sulfonylurea herbicides, triazolopyrimidine herbicides, pyrimidinyloxybenzoate herbicides, sulfonylamino-carbonyltriazolinone herbicides, and combinations and mixtures thereof.

5. The rice seed of claim 3, wherein said AHAS-inhibiting herbicide is an imidazolinone herbicide or a mixture of two or more imidazolinone herbicides.

6. The rice seed of claim 5, wherein the imidazolinone herbicide is selected from the group consisting of 2-(4-isopropyl-4-methyl-5-oxo-2-imidazolin-2-yl)-nicotinic acid, 2-(4-isopropyl-4-methyl-5-oxo-2-imidazolin-2-yl)-3-quinolinecarboxylic acid, 5-ethyl-2-(4-isopropyl-4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, 2-(4-isopropyl-4-methyl-5-oxo-2-imidazolin-2-yl)-5-methylnicotinic acid, mixtures of methyl-6-(4-isopropyl-4-methyl-5-oxo-2-imidazolin-2-yl)-m-toluate and methyl-2-(4-isopropyl-4-methyl-5-oxo-2-imidazolin-2-yl)-p-toluate, imazapyr, imazapic, imazethapyr, imazamox, imazamethabenz, and imazaquin herbicides, and mixtures thereof.

7. A rice plant, or a part thereof, produced by growing the seed of claim 1.

8. Pollen or an ovule of the plant of claim 7.

9. A method for producing rice plants, said method comprising planting a plurality of rice seeds as recited in claim 1 under conditions favorable for the growth of rice plants.

10. The method of claim 9, further comprising the step of producing rice seed from the resulting rice plants.

11. A rice seed produced by the method of claim 10.

12. A method for combating undesired vegetation or controlling weeds in the vicinity of a rice plant of rice cultivar CLL18, comprising contacting the rice seed of claim 1 with an AHAS-inhibiting herbicide before sowing and/or after pregermination.

13. The method of claim 12, wherein said AHAS-inhibiting herbicide is selected from the group consisting of imidazolinone herbicides, sulfonylurea herbicides, triazolopyrimidine herbicides, pyrimidinyloxybenzoate herbicides, sulfonylamino-carbonyltriazolinone herbicides, and combinations and mixtures thereof.

14. The method of claim 13, wherein said AHAS-inhibiting herbicide is an imidazolinone herbicide or a mixture of two or more imidazolinone herbicides.

15. A method for combating undesired vegetation or controlling weeds in the vicinity of a rice plant of rice cultivar CLL18, comprising applying an effective amount of at least one AHAS-inhibiting herbicide to the weeds and to the rice plant, a representative sample of seed of said cultivar having been deposited under ATCC National Center for Marine Algae and Microbiota International Depositary Authority Accession No. 202305002.

16. The method of claim 15, wherein said AHAS-inhibiting herbicide is selected from the group consisting of imidazolinone herbicides, sulfonylurea herbicides, triazolopyrimidine herbicides, pyrimidinyloxybenzoate herbicides, sulfonylamino-carbonyltriazolinone herbicides, and combinations and mixtures thereof.

17. The method of claim 16, wherein said AHAS-inhibiting herbicide is an imidazolinone herbicide or a mixture of two or more imidazolinone herbicides.

18. The method of claim 16, wherein said imidazolinone herbicide is selected from the group consisting of 2-(4-isopropyl-4-methyl-5-oxo-2-imidazolin-2-yl)-nicotinic acid, 2-(4-isopropyl-4-methyl-5-oxo-2-imidazolin-2-yl)-3-quinolinecarboxylic acid, 5-ethyl-2-(4-isopropyl-4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, 2-(4-isopropyl-4-methyl-5-oxo-2-imidazolin-2-yl)-5-methylnicotinic acid, mixtures of methyl-6-(4-isopropyl-4-methyl-5-oxo-2-imidazolin-2-yl)-m-toluate and methyl-2-(4-isopropyl-4-methyl-5-oxo-2-imidazolin-2-yl)-p-toluate, imazapyr, imazapic, imazethapyr, imazamox, imazamethabenz, and imazaquin herbicides and mixtures thereof.

19. A tissue culture of regenerable cells or protoplasts produced from the rice plant, or a plant part of claim 7.

20. The tissue culture of claim 19, wherein said cells or protoplasts are produced from a tissue selected from the group consisting of embryos, meristematic cells, pollen, leaves, anthers, roots, root tips, pistils, anthers, cotyledon, hypocotyl, glumes, panicles, flowers, seeds, and stems.

21. A rice plant regenerated from the tissue culture of claim 19, said rice plant having all the morphological and physiological characteristics of CLL18.

22. A method for producing an herbicide-resistant rice hybrid plant, said method comprising crossing a first parent rice plant with a second parent rice plant, wherein the first parent rice plant is the rice plant of claim 7, and optionally wherein the second parent rice plant is not resistant to an herbicide.

23. The method of claim 22, further comprising selecting for a progeny rice plant that is resistant to at least one AHAS-inhibiting herbicide.

24. The method of claim 23, wherein said AHAS-inhibiting herbicide is an imidazolinone herbicide or a mixture of two or more imidazolinone herbicides.

25. An herbicide-resistant rice plant or plant part produced by the method of claim 22.

26. The method of claim 22, further comprising the step of producing rice seed from the resulting rice plants.

27. The method of claim 22, wherein the second parent rice plant is transgenic.

28. A method comprising transforming the rice plant of claim 7 or cell thereof with a transgene, wherein the transgene confers at least one trait selected from the group consisting of: herbicide resistance; insect resistance; resistance to bacterial, fungal, or viral disease; modified fatty acid metabolism; modified carbohydrate metabolism; and male sterility.

29. A rice plant or part thereof, or rice seed, produced by the method of claim 28.

30. A method of introducing a desired trait into rice cultivar CLL18, said method comprising the steps of:

(a) crossing plants as recited in claim 7 with plants of another rice line expressing the desired trait, to produce progeny seeds;

(b) growing progeny seeds to produce progeny plants and selecting progeny plants that express the desired trait, to produce selected progeny plants;

(c) crossing the selected progeny plants with plants of rice cultivar CLL18 to produce new progeny plants;

(d) selecting new progeny plants that express both the desired trait and some or all of the physiological and morphological characteristics of rice cultivar CLL18, to produce new selected progeny plants; and (e) repeating steps (c) and (d) three or more times in succession, to produce selected higher generation back-cross progeny plants that express the desired trait.

31. The method of claim 30, wherein the desired trait is selected from the group consisting of: herbicide resistance traits; insect resistance traits; traits of resistance to bacterial, fungal, or viral disease; modified fatty acid metabolism traits; modified carbohydrate metabolism traits; and male sterility traits.

32. The method of claim 31, wherein the desired trait is herbicide resistance traits and an AHAS-inhibiting herbicide is applied to the progeny seeds or the progeny plants in step (b) to select for herbicide resistant plants and wherein the AHAS-inhibiting herbicide is selected from the group consisting of imidazolinone herbicides, sulfonylurea herbicides, triazolopyrimidine herbicides;

pyrimidinyloxybenzoate herbicides, sulfonylamino-carbonyltriazolinone herbicides, and combinations and mixtures thereof.

* * * * *